United States Patent [19]

Dingle et al.

[11] 4,427,649
[45] Jan. 24, 1984

[54] PHARMACEUTICAL COMPOSITIONS

[75] Inventors: John T. Dingle, Whittlesford; John L. Gordon, Cambridge; Geraint Jones, Macclesfield; Clive G. Knight, Huntingdon; John S. Lowe, Wilmslow, all of England

[73] Assignees: Imperial Chemical Industries Limited; National Research Development Corporation, both of London, England

[21] Appl. No.: 336,167

[22] Filed: Dec. 31, 1981

Related U.S. Application Data

[63] Continuation of Ser. No. 777,427, Mar. 14, 1977, abandoned.

[30] Foreign Application Priority Data

Mar. 19, 1976 [GB] United Kingdom ............... 11147/76

[51] Int. Cl.$^3$ .......................... A61K 9/16; A61K 9/42; A61K 31/575; A61K 47/00
[52] U.S. Cl. ...................................... 424/38; 424/238; 424/241; 424/242; 424/243
[58] Field of Search ........................... 424/38, 238-243

[56] References Cited

FOREIGN PATENT DOCUMENTS 2249552  5/1973  Fed. Rep. of Germany .
2532317  1/1976  Fed. Rep. of Germany .

OTHER PUBLICATIONS

Hollander (1955) Ann. N.Y. Acad. Sci. 61: 511–516, the Use of Intra-Articular Hydrocortisone, its Analogs and its Higher Esters in Arthritis.
Hollander (1972)"Arthritis and Allied Conditions" Hollander, J. L. and McCarthy, D. J. Eds. 8th Ed. p. 517-534 Lea and Fibiger, Philadelphia, Pa.
Goetzel et al., (Goetzel) Ann. Rheum. Dis. 33: 62–66 (1974) Effects of Intra–Articular Corticosteroids in Vivo on Synovial Fluid Variables in Rheumatoid Synovitis.
Shaw et al., (Shaw) Biochem. J. (1976) 158: 473–476 "Lipo Somal Retention of a Modified Anti–Inflammatory Steroid".
Segal et al., (Segal) Clinical Science & Molecular Medicine 49: 99–106 (1975) Liposomes as Vehicles for the Local Release of Drugs.
Stevens et al., (Stevens) CA. 78, No. 79949H (1973) of F.E.B.S. Lett. (1972) 27(1) 145-148, "Effect of Side Chain Structure on the Incorporation of Steroids into Lipid Bilayers (Liposomes)".
Heap et al., (Heap), Ca.74, No. 72170F (1971) to Biochem. Biophys. Acta. (1970) 218 (3): 482–495, "Steroids and their Interactions with Phospholipids, Solubility, Distribution Coefficient and Effect on Potassium Permeability of Liposomes".
Smith et al., (Smith) Ca. 82, No. 13324ot (1975) of Biochem. Soc. Trans. (1974) 2(5): 962-963 Nuclear Magnetic Resonance Studies of Phospholipid–Steroid Relations in Lipid Bilayers.

Primary Examiner—Shep K. Rose
Attorney, Agent, or Firm—Cushman, Darby & Cushman

[57] ABSTRACT

Pharmaceutical liposome compositions containing an anti-inflammatory steroid derivative bearing a lipophilic substituent, for example cortisol 21-hexadecanoate. Method of treatment of inflammation at a site involving an enclosed cavity, for example the treatment of rheumatic disease, comprising injecting a said pharmaceutical liposome composition into said cavity. Specified new steroid derivatives, for example fluocinolone acetamide 21-hexadecanoate.

8 Claims, No Drawings

PHARMACEUTICAL COMPOSITIONS

This is a continuation, of application Ser. No. 777,427 filed Mar. 14, 1977, abandoned.

This invention relates to pharmaceutical compositions and more particularly it relates to the formulation of substances for the treatment of inflammation at sites involving an enclosed cavity, for example inflammation in synovial joints such as occurs in rheumatic diseases.

The inflammation which is a feature of the rheumatic diseases is treated clinically by the use of various drugs. However, the adverse side effects of these drugs often limit their use, particularly in the long term therapy required in chronic rheumatic disease. Furthermore, although it is known to treat inflammation at sites involving an enclosed cavity by directly administering an active substance into said cavity, it has been found that the active substance escapes relatively easily from said cavity, thus reducing the therapeutic effect.

In recent years there has been an increasing interest in the use of liposomes as carriers of drugs and enzymes, and also as immunological adjuvants. Liposomes are quite widely described in the literature and their general structure is well known; they are onion-like structures comprising a series of lipid layers spaced one from another by aqueous material, with the outermost layer being lipid. Liposome carrier formulations are generally administered intravenously, subcutaneously or orally, and they have the advantage that enclosure of a drug within a liposome limits the level of any physiological effect produced by the drug before it reaches its desired site of action.

According to the invention there is provided a pharmaceutical composition comprising liposomes containing an anti-inflammatory steroid derivative which bears a lipophilic substituent.

By administering the liposomes of this invention directly into an enclosed cavity in which an inflammation exists, it is possible to effect an increased level of retention of the agent at the required site of action, thereby both obtaining increased advantage from its action against the inflammation and restricting the level of any side effects. Whilst the present invention finds particular application in the treatment of rheumatic diseases when the liposomes are administered intra-articularly, it is also applicable in the treatment of inflammation at other sites involving an enclosed cavity, for example the eye, lung, testis and peritoneum.

The initial stages of the preparation of liposomes according to the present invention may conveniently follow procedures described in the art, i.e. the lipid starting materials being dissolved in a solvent which is then evaporated and the resultant lipid layer then being dispersed in the selected aqueous medium. In contradistinction to the usual practice, however, it is preferred not to sonicate the liposomes thus produced, since this reduces their size. The liposomes produced by such a procedure will usually be of a range of sizes. The liposomes of this invention preferably have a diameter greater than 100 nm., more preferably they have a diameter greater than 250 nm., and even more preferably they have a diameter greater than 500 nm. It is known, for example, that liposomes having a diameter of up to 5000 nm. may be readily phagocytosed. It is thus preferred that the liposomes prepared by said art procedure are fractionated to remove substantially all those having a diameter less than 100 nm., and preferably also those having a diameter less than 250 nm., and, even more preferably, also those having a diameter less than 500 nm. Fractionation may conveniently be effected by molecular sieve chromatography; the size of the sieve being selected according to the desired liposome size.

A wide variety of lipid materials may be used to form the liposomes, but lipids which are non-immunogenic and bio-degradable are preferred. The properties of the lipid, for example its phase transition temperature, can have a marked effect on the retention and uptake of the liposomes in the enclosed cavity and for this reason the well defined synthetic lecithins are preferred to the natural lecithins. Examples of synthetic lecithins which may be used, together with their respective phase transition temperatures, are di-(tetradecanoyl)phosphatidylcholine (23° C.), di-(hexadecanoyl)phosphatidylcholine (41° C.) and di-(octadecanoyl)phosphatidylcholine (55° C.). Other synthetic lecithins which may be used are unsaturated synthetic lecithins, for example di-(oleyl)phosphatidylcholine and di-(linoleyl)phosphatidylcholine. Preferred synthetic lecithins are di-(hexadecanoyl)phosphatidylcholine and di-(octadecanoyl)phosphatidylcholine (the latter optionally together with an unsaturated lecithin such that the mixture has a phase transition temperature lower than that of said octadecanoyl derivative, for example a phase transition temperature in the range 35°–45° C.). According to one preferred embodiment of the invention there is used a mixture of lecithins, and in particular a mixture of synthetic lecithins, which is adapted to afford a sustained release of the steroid derivative within the enclosed cavity. In addition to the main liposome-forming lipid or lipids, which are usually phospholipids, other lipids may be included, for example cholesterol may be used to modify the structure of the liposome membrane, rendering it more fluid or more rigid depending on the nature of the main liposome-forming lipid or lipids. An optional third component is a material which provides a negative charge, for example phosphatidic acid, dicetyl phosphate or beef brain ganglioside, or one which provides a positive charge, for example stearylamine acetate.

A suitable steroid derivative for use according to this invention is an anti-inflammatory corticosteroid which has been chemically modified in that it bears a lipophilic substituent. The corticosteroid (prior to said modification) may, for example, be corticosterone or cortisol (i.e. hydrocortisone or 17-hydroxycorticosterone), or a derivative of any of these compounds, including the $\Delta^1$-dehydro or 9-fluoro derivative, for example prednisolone ($\Delta^1$-dehydrocortisol), methylprednisolone (6$\alpha$-methyl-$\Delta^1$-dehydrocortisol), paramethasone (6$\alpha$-fluoro-16$\alpha$-methylprednisolone), fluocinolone acetonide (6$\alpha$,9$\alpha$-difluoro-16$\alpha$-hydroxyprednisolone 16,17-acetonide), fludrocortisone acetate (9$\alpha$-fluorocortisol 21-acetate), triamcinolone (9$\alpha$-fluoro-16$\alpha$-hydroxy-$\Delta^1$-dehydrocortisol), or dexamethasone (9$\alpha$-fluoro-16$\alpha$-methyl-$\Delta^1$-dehydrocortisol). A preferred group consists of anti-inflammatory corticosteroids bearing an 11-hydroxy substituent.

Attachment of the lipophilic substituent at the 21-position of a steroid is preferred, where appropriate, although attachment at other ring positions, for example at the 11- or 17-position, may also be considered. The substituent conveniently derives its lipophilic character from the presence therein of a hydrocarbon chain which may be cyclic or acyclic but is more usually aliphatic rather than aromatic in nature. The hydrocarbon chain may carry substituents and may be interrupted by the presence of at least one hetero atom, for example an oxygen atom, but conveniently contains at least 4 and preferably 6 to about 25 carbon atoms. Attachment of the substituent is conveniently effected through a suitable functional grouping which is inserted into, or preferably is already present in, the compound. A particularly convenient functional grouping for this purpose is the hydroxy group, and the lipophilic substituent will often be attached to the steroid ring system, for example, by the residue of such a group or of some group incorporating a hydroxy group, for example —CO—CH$_2$—OH. Attachment of the substituent to the hydroxy group may conveniently be effected through the formation of an ether or a carboxylic or carbamoyl ester linkage, the substituent then conveniently comprising an alkyl group R—, an alkanoyl group RCO— or a substituted carbamoyl group RNHCO—. The alkyl group R may in each case be cyclic, for example cyclohexyl, but is preferably acyclic, which may be straight-chained or branched, and saturated and unsaturated. Such a group R may be a butyl, pentyl, hexyl, heptyl, octyl, nonyl, decyl, undecyl, dodecyl, tridecyl, tetradecyl, pentadecyl, hexadecyl, heptadecyl or octadecyl group, the groups of at least 7 or 8, and particularly of 15, 16 or 17, carbon atoms being of especial interest. Particularly preferred compounds contain an alkanoyl group of 16 or 18 carbon atoms; i.e. a hexadecanoyl or octadecanoyl group.

As indicated above, steroids modified at the 21 position are of particular interest, and examples of such steroids are those, for example cortisol, containing the following side chains linked to the 17 position (it is to be understood that the initial —COCH$_2$O— group in the following side chains corresponds to the —COCH$_2$OH group substituted at the 17 position in cortisol itself):

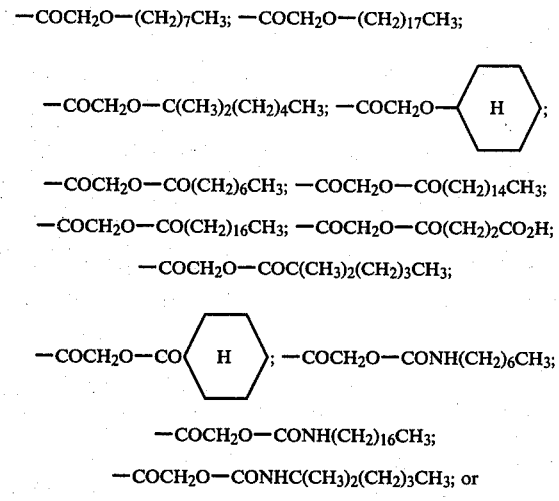

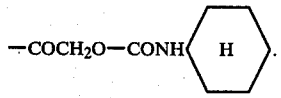

A particularly preferred group of steroids for use in the liposomes of this invention consists of anti-inflammatory corticosteroids bearing an 11-hydroxy substituent and bearing a lipophilic substituent which is attached by means of a carboxylic ester linkage to the residue of a hydroxy group which itself is attached to the 21-position of the corticosteroid, the said lipophilic substituent comprising an acyclic aliphatic chain of 7 to 18 carbon atoms.

Many of the said modified steroid derivatives are new compounds, and these compounds constitute another feature of this invention. Specific new compounds of the invention are: cortisol 21-(2-methyl-dodecanoate), cortisol 21-cyclopentylacetate, cortisol 21-(2-ethyl-hexanoate), prednisolone 21-hexadecanoate, fluocinolone acetonide 21-hexadecanoate, and dexamethasone 21-hexadecanoate.

The said modified steroid derivatives are obtainable by conventional synthetic procedures for effecting the attachment of lipophilic substituents of the type described, for example the esterification or etherification of hydroxy groups, or by obvious chemical equivalents of such methods. Thus, for example, esterification with a carboxylic acid may be effected by reaction of the hydroxy group of a steroid with the free acid, usually in the presence of a suitable condensing agent such as a carbodiimide, or with a suitable acid functional derivative, for example the anhydride or halide, whilst esterification with a substituted carbamic acid may be effected by reaction with an isocyanate. Suitable etherification procedures include reaction of a hydroxy group, in the form of a sodio derivative (—O$^\ominus$Na$^\oplus$), with a halide.

Liposome preparations according to the present invention are most usually administered directly into the enclosed cavity in which the inflammation exists. Thus, particles of a size greater than about 250 nm. cannot readily escape from synovial joints, and the synovial fixed macrophages are capable of readily phagocytosing the liposomes injected into the joint so that the majority of the pharmacologically active material injected reaches the cells for which it is intended. This means that much lower doses can be used compared with the conventional dose of the steroid when administered by a conventional procedure (thereby reducing any likelihood of undesirable side effects). While the dosage will depend on the particular modified steroid derivative which is used, levels of as little as 1 mg. down to 50 μg., or even less, are often sufficient. It will be appreciated that the nature of this particular method of formulation may also permit the administration of substances which are too toxic to administer by conventional methods.

Applications of the compositions of the present invention to other than rheumatic diseases include the treatment by topical application of certain inflammatory diseases of the eye, aerosol application to the lung for allergic and otherwise caused inflammation, and intercavity injections for inflammatory changes in the testis or peritoneum.

The invention is illustrated but not limited by the following Examples:

EXAMPLE 1

(a) (i) Synthetic di-(hexadecanoyl)phosphatidylcholine (8 mg.), phosphatidic acid (1 mg.) and cortisol 21-octanoate (1 mg.) in chloroform (1 ml.) were mixed with chloroform (1.25 ml.) in a pear-shaped flask. The solvent was then removed by rotary evaporation in vacuo at a temperature of about 61° C. (being 20° C. above the phase transition temperature for the lecithin). The thin lipid film thereby produced on the walls of the flask was dispersed by regular vigorous shaking in 5 mM phosphate-buffered saline (pH 7.35; 1 ml.) at the same temperature as that of the rotary evaporation. The phosphate-buffered saline was prepared as follows:

The following salts were dissolved in distilled water (2.5 l.):

| Sodium chloride | 106.25 g. |
|---|---|
| Disodium hydrogen orthophosphate | 40.20 g. |
| Sodium dihydrogen orthophosphate | 1.95 g. |

The resulting solution was adjusted to pH 7.35 with 6 N-hydrochloric acid. This stock solution was then diluted as follows:

| Stock phosphate-buffered saline | 100 ml. |
|---|---|
| Distilled water | 1.9 l. |
| Sodium chloride | 12.75 g. |

These ingredients were mixed to produce 5 mM phosphate-buffered saline (pH 7.35).

The resulting liposome suspension was allowed to stand for 1 hour at room temperature, and the liposomes were then washed three times with 5 mM phosphate-buffered saline (pH 7.35; 1 ml.) before being placed on a 30 cm.×1.5 cm. column packed with Control-Pore glass beads (50–100 mesh; theoretical exclusion limit of 250 nm.) pretreated with 1% w/w Carbowax 20 M, the column being standardised before use with latex particles of known size. The column was eluted with the 5 mM phosphate-buffered saline and the fractions emerging were monitored by absorbance spectrophotometry at 410 nm. The liposome-containing fractions consisted of vesicles between 500 to 5000 nm. in diameter as assessed by (i) electron microscopy; (ii) light microscopy following acridine orange staining and standardisation with latex beads of a known diameter; and (iii) distribution in a Coulter counter with a 30,000 nm. tube, again using latex beads of a known size as a standard.

The cortisol 21-octanoate used in the above Example may be obtained as follows:

Cortisol (50 mg.) in pyridine (1 ml.) at 0° C. was treated with octanoyl chloride (0.05 ml.), and, after reaction for 16 hours during which the temperature rose to room temperature, the solvent was removed in vacuo at 40° C. The residue was dissolved in chloroform (10 ml.) and washed in turn with 3×10 ml. portions of the following aqueous solutions: 1/10th saturated sodium chloride, saturated sodium bicarbonate, 10% w/v citric acid, and 1/10th saturated sodium chloride, and finally with water. The chloroform solution was then dried over magnesium sulphate and evaporated to dryness in vacuo at 40° C. to give cortisol 21-octanoate, m.p. 115°–116° C.

Esters with other monocarboxylic acids, including hexadecanoic acid and cyclohexane carboxylic acid, are prepared by an analogous procedure to that described immediately above using a 2-fold excess of the appropriate acid chloride in pyridine, whilst esters with substituted carbamic acids, including N-octylcarbamic acid, are prepared by a similar procedure in which the appropriate isocyanate is used rather than the acid chloride.

(ii) In a variation of the procedure described in Example 1 (a)(i) the di-(hexadecanoyl)phosphatidylcholine was replaced by an alternative lecithin, for example di-(tetradecanoyl)- or di-(octadecanoyl)phosphatidylcholine.

(iii) In a variation of the procedure described in Example 1 (a)(i) or 1 (a)(ii) the cortisol 21-octanoate was replaced by an equal weight of cortisol 21-cyclohexane carboxylate (m.p. 199°–201° C.).

(b) The procedure described in Example 1 (a)(i), (ii) or (iii) was varied by replacing the phosphatidic acid (1 mg.) with stearylamine.

(c) The procedure described in Example 1 (a)(i), (ii) or (iii) was varied by omitting the phosphatidic acid.

EXAMPLE 2

For these tests liposomes were prepared substantially as described in Example 1 (a)(i), but using a radioactively labelled steroid, i.e. [1,2,6,7(n)-$^3$H]-cortisol 21-octanoate, and also incorporating as additional markers $^{35}$S (present as $SO_4^{--}$) for the aqueous phase and $^{125}$I labelled N-octadecyl-3-(4-hydroxyphenyl)propionamide ("OHP") for the lipid phase.

The liposome suspension (1 ml.) was diluted ten-fold in 5 mM phosphate buffered saline (pH 7.35), and incubated at 37° C. The buffer was changed every 24 hours following centrifugation, and the rate of removal of the various markers was studied. Typically, both the phase markers and the [1,2,6,7(n)-$^3$H]-cortisol 21-octanoate were retained within the liposome for several days.

EXAMPLE 3

Liposomes containing [1,2,6,7(n)-$^3$H]-cortisol 21-octanoate were administered to synovial cells cultured in vitro and the uptake of the liposomes was followed through the radioactive marker and by cytochemical observation. The cells typically showed prolonged biochemical changes, including diminished mitotic activity and decrease in proteolytic enzyme synthesis and secretion.

EXAMPLE 4

A mixed unfractionated population of liposomes, prepared substantially as described in Example 1 (a)(i) but omitting the steroid and incorporating $^{125}$I labelled OHP in the lipid phase, was administered intra-articularly to one normal and one arthritic joint of monoarthritic rabbits. In the arthritic joint, in distinction to the normal joint, a significant amount of the marker was found to be associated with the joint after a period of 3 hours. This preferential association of marker with the diseased joint was still apparent 6 days after the intra-articular administration and amounted to more than 30% of the amount administered.

EXAMPLE 5

In these tests twenty rabbits were employed having the so-called Page-Thomas model arthritis induced by polylysine (see Example 21). Neutral liposomes (1 mg.) prepared substantially as described in Example 1 (c) from di-(hexadecanoyl)phosphatidylcholine, and containing 100 μg. of cortisol 21-octanoate, were administered to an arthritic joint of these rabbits, when 30% of the steroid was typically found to be retained within the joint. The administration typically resulted in decreased lysosomal enzyme secretion by the joint back to control levels and a reduced inflammatory reaction which was histologically demonstrable.

EXAMPLE 6

Hexadecanoyl chloride (0.5 ml.) was added to a stirred solution of cortisol (0.5 g.) in freshly distilled pyridine (10 ml.) at 0° C., and the mixture was stirred overnight at 0° C. Further hexadecanoyl chloride (0.5 ml.) was then added and the mixture was stirred for 18 hours at ambient temperature. The mixture was mixed with 2 N-hydrochloric acid (50 ml.) and then extracted with ethyl acetate (3×50 ml.). The combined organic extracts were washed successively with saturated sodium bicarbonate solution (50 ml.), water (50 ml.), and saturated brine (50 ml.), and then dried over anhydrous magnesium sulphate. The solvent was evaporated in vacuo and the residue was crystallised from aqueous methanol to give cortisol 21-hexadecanoate (pregn-4-ene-3,20-dione-11β,17α-dihydroxy-21-hexadecanoate), m.p. 104°–106° C.

EXAMPLE 7

Synthetic di-(hexadecanoyl)phosphatidylcholine (14.9 mg.), phosphatidic acid (2 mg.) and cortisol 21-hexadecanoate (1.66 mg.) were mixed in chloroform (2 ml.) in a round-bottomed flask. The solvent was allowed to evaporate while the flask was rotated gently by hand, and the final traces of chloroform were removed with a stream of nitrogen blow into the flask. 5 mM phosphate-buffered saline (pH 7.4; 5 ml.) was added to the flask, which was heated to 70° C. on a water bath.

The phosphate-buffered saline consisted of the following:

| | |
|---|---|
| Disodium hydrogen orthophosphate dihydrate | 3.22 g. |
| Sodium dihydrogen orthophosphate | 0.156 g. |
| Sodium chloride | 18 g. |
| Distilled water | to 2 liters |

If the pH was not 7.4, it was adjusted to that value with N-sodium hydroxide or N-hydrochloric acid.

The lipid film was then dispersed by vibrating the flask on a vibratory mixer to give a dispersion of liposomes containing cortisol 21-hexadecanoate. The contents of the flask were transferred to a 25 ml. ultracentrifuge tube, made up to 25 ml. with 5 mM phosphate-buffered saline (pH 7.4), and the liposomes were spun down by ultra-centrifugation at 120,000 g. for 60 minutes. The supernatant liquid was removed and replaced by fresh buffer, and the liposomes were re-dispersed at 70° C. on the vibratory mixer. After ultra-centrifugation as above, the procedure was repeated and the liposome sediment was finally dispersed in the buffer (5 ml.). There was thus obtained a dispersion of negatively charged liposomes containing cortisol 21-hexadecanoate.

EXAMPLE 8

Liposomes were prepared in a 250 ml. round-bottomed flask which had been thoroughly cleaned with chromic acid, repeatedly rinsed with distilled water followed by methanol, and finally rinsed with chloroform. Di-(hexadecanoyl)phosphatidylcholine (14.9 mg.), stearylamine acetate (0.95 mg.) and [1,2,6,7(n)-$^3$H]-cortisol 21-hexadecanoate (1.66 mg.)[specific activity 67.4 μCi/g.] were added as chloroform solutions to the flask in a total volume of 2.5 ml. The chloroform was slowly evaporated by rotating the flask by hand to form a uniform mixed steroid/lipid film on the walls of the flask, and the final traces of chloroform were removed from the film by blowing a stream of dry nitrogen gas into the flask for several minutes. 5 mM phosphate buffer (see below; pH 7.4; 5 ml.) was added to the flask, and the flask and its contents were heated to approximately 70° C. in a water bath. The lipid film was immediately dispersed to form liposomes by agitation of the hot mixture on a bench vibromixer. Heating was necessary as the liposomes could only be formed at a temperature above the crystal⟷liquid crystal transition temperature of the phospholipid [Tc], which in the case of di-(hexadecanoyl)phosphatidylcholine is 41° C. The radioactivity of the liposome suspension, before washing, was measured by dispersing duplicate 50 μl. samples of the suspension in 10 μl. of a triton/toluene scintillant solution and counting the radioactivity with a liquid scintillation counter.

The liposome suspension was then washed by diluting it to 25 ml. with 5 mM phosphate buffer (pH 7.4) and ultracentrifuging at 275,000 g. for 60 minutes. The clear supernatant liquid was removed from the tube, and the liposome plug was again washed by re-dispersing it above 41° C. in 5 mM phosphate buffer (pH 7.4; 25 ml.) and ultracentrifuging as before. The resulting liposome plug was finally dispersed to 5 ml. with 5 mM phosphate-buffered saline (pH 7.4), heated at 50°–100° C. The activity of the liposome suspension after washing was measured by scintillation counting of duplicate 50 μl. samples as the dispersion as before. The incorporation of the cortisol 21-hexadecanoate into the di-(hexadecanoyl)phosphatidylcholine liposomes was calculated from the ratio of the activities of the suspension before and after washing, and was 88% of the total amount of drug added to the preparation.

The above-mentioned 5 mM phosphate buffer (pH 7.4) consisted of the following:

| | |
|---|---|
| Disodium hydrogen orthophosphate dihydrate | 3.22 g. |
| Sodium dihydrogen orthophosphate | 0.156 g. |
| Distilled water | to 2 liters |

If the pH was not 7.4, it was adjusted to that value with N-sodium hydroxide or N-hydrochloric acid.

EXAMPLE 9

The procedure described in Example 8 was repeated except that the stearylamine acetate was replaced by phosphatidic acid (2 mg.). There were thus obtained negatively charged liposomes. The incorporation of the cortisol 21-hexadecanoate into these liposomes was 97% of the total amount of drug added to the preparation.

EXAMPLE 10

A 250 ml. round-bottomed flask was prepared as described in Example 8. Egg lecithin (16.1 mg.), stearylamine acetate (0.95 mg.) and [1,2,6,7(n)-$^3$H]-cortisol 21-hexadecanoate (1.66 mg.) [specific activity 67.4 μCi/g.] were then added to the flask as chloroform solutions in a total volume of 2.5 ml. The procedure for liposome formation, washing and assay was then similar to that described in Example 8 except that in this Example the lipid-steroid mixture was dispersed at all stages of the preparation and purification at room temperature. This was because the crystal⟷liquid crystal transition temperature for egg lecithin is below room temperature. The incorporation of the cortisol 21-hexadecanoate into egg lecithin liposomes was 86% of the added amount of drug.

EXAMPLE 11

The procedure described in Example 10 was repeated except that the stearylamine acetate was replaced by phosphatidic acid (2 mg.). The incorporaton of the cortisol 21-hexadecanoate into these liposomes was 57% of the total amount of drug added to the preparation.

EXAMPLE 12

Liposomes containing cortisol 21-octanoate were prepared from several phospholipids using essentially similar methods to those described in Examples 8 to 11. The relevant details, including the temperature at which the lipid must be dispersed, are given in Table 1.

TABLE 1

| Preparation | Neutral lipid and weight (mg.) | Charged lipid and weight (mg.) | Weight of cortisol derivative (mg.) | Dispersion temperature (°C.) | Relevant Example | Steriod incorporated (%) |
| --- | --- | --- | --- | --- | --- | --- |
| a | HPC 14.9 | SA 0.95 | 0.81 | 50–100 | 8 | 90 |
| b | HPC 14.9 | PTA 2 | 1 | 50–100 | 9 | 34 |
| c | EL 16.1 | PTA 2 | 1 | room temperature | 11 | 79 |
| d | OPC 16 | PTA 2 | 1 | room temperature | 11 | 75 |

HPC — di-(hexadecanoyl)phosphatidylcholine
EL — egg lecithin
OPC — di-oleylphosphatidylcholine
SA — stearylamine acetate
PTA — phosphatidic acid

EXAMPLE 13

Liposomes containing cortisol 21-butyrate were prepared using essentially similar methods to those described in Examples 8 to 11. The relevant details are given in Table 2.

TABLE 2

| Preparation | Neutral lipid and weight (mg.) | Charged lipid and weight (mg.) | Weight of cortisol derivative (mg.) | Dispersion temperature (°C.) | Relevant Example | Steriod incorporated (%) |
| --- | --- | --- | --- | --- | --- | --- |
| a | HPC 14.9 | SA 0.95 | 0.65 | 50–100 | 8 | 15 |
| b | HPC 14.9 | PTA 2 | 0.65 | 50–100 | 9 | 8 |
| c | EL 16.9 | SA 0.95 | 0.65 | room temperature | 10 | 38 |
| d | EL 16.9 | PTA 2 | 0.65 | room temperature | 11 | 27 |

EXAMPLE 14

In a similar manner to that described in Example 6, but using the crystallisation solvent indicated below, the following compounds were obtained using the appropriate starting materials:

cortisol 21-(2-methyl-dodecanoate), m.p. 55°–58° C. (methanol);

cortisol 21-cyclopentylacetate, m.p. 178°–180° C. (ethyl acetate);

cortisol 21-(2-ethyl-hexanoate), m.p. 120°–123° C. (no crystallisation solvent used); and prednisolone 21-hexadecanoate, m.p. 115°–116° C. (aqueous methanol).

EXAMPLE 15

Hexadecanoyl chloride (0.4 ml.) was added to a stirred solution of fluocinolone acetonide (0.2 g.) in freshly distilled pyridine (8 ml.). The mixture was kept at room temperature overnight, and then mixed with water (15 ml.) and extracted with diethyl ether (3×50 ml.). The combined ethereal extracts were successively washed with water (7×20 ml.), 2% w/v hydrochloric acid (50 ml.) and saturated sodium bicarbonate (50 ml.), and then dried with anhydrous magnesium sulphate.

The solvent was evaporated in vacuo, and the residue purified by preparative thin layer chromatography using 1:1 v/v toluene:ethyl acetate as the developing solvent. There was thus obtained fluocinolone acetonide 21-hexadecanoate, m.p. 54°–55° C.

In a similar manner, using dexamethasone as the steroidal starting material, there was obtained dexamethasone 21-hexadecanoate, m.p. 48°–50° C.

EXAMPLE 16

The procedure described in Example 10 was repeated but using cortisol 21-pivalate (1.2 mg.), egg lecithin (16.1 mg.) and phosphatidic acid (2 mg.). There were thus obtained negatively charged liposomes. The incorporation of the steroid derivative into these liposomes was 7% of the total amount added to the preparation.

EXAMPLE 17

Liposomes containing fluocinolone acetonide 21-hexadecanoate were prepared using essentially similar methods to those described in Examples 8 and 9. The relevant details are given in Table 3.

TABLE 3

| Preparation | Weight of HPC (mg.) | Charged lipid and weight (mg.) | Weight of steroid (mg.) | Dispersion temperature (°C.) | Relevant Example | Steroid incorporated (%) |
|---|---|---|---|---|---|---|
| a | 14.9 | SA 0.95 | 0.99 | 50–100 | 8 | 83 |
| b | 14.9 | PTA 2 | 0.99 | 50–100 | 9 | 85 |

EXAMPLE 18

Liposomes containing dexamethasone 21-hexadecanoate were prepared using essentially similar methods to those described in Examples 8 and 9. The relevant details are given in Table 4.

TABLE 4

| Preparation | Weight of HPC (mg.) | Charged lipid and weight (mg.) | Weight of steroid (mg.) | Dispersion temperature (°C.) | Relevant Example | Steroid incorporated (%) |
|---|---|---|---|---|---|---|
| a | 14.9 | SA 0.95 | 0.95 | 50–100 | 8 | 93 |
| b | 14.9 | PTA 2 | 0.95 | 50–100 | 9 | 88 |

EXAMPLE 19

The incorporation of cortisol 21-hexadecanoate into the phospholipid phase of di-(hexadecanoyl)phosphatidylcholine liposomes can be demonstrated by differential scanning calorimetry of the liposomes. These experiments were carried out to show that in such liposomes cortisol 21-hexadecanoate is molecularly dispersed in the phospholipid and that the liposome suspension is not a mixture of liposomes and discrete steroid particles. The technique relies on the fact that hydrated phospholipids which form liposomes exhibit an endothermic transition from crystal to liquid crystaline phases and that this endotherm can be readily detected by differential scanning calorimetry (hereinafter "DSC"). Compounds such as cholesterol, which are known to be incorporated in, for example, biological membranes, are also known to alter the transition temperature of the phospholipids in these membranes including di-(hexadecanoyl)phosphatidylcholine. The DSC spectra of liposomes containing cortisol 21-hexadecanoate have therefore been compared with the spectra of hydrated physical mixtures of di-(hexadecanoyl)phosphatidylcholine and cortisol 21-hexadecanoate. The results show significant differences between the liposomes and the mixtures and suggest that in liposomes the steroid is molecularly dispersed in the phospholipid.

A series of neutral di-(hexadecanoyl)phosphatidylcholine liposome samples containing increasing amounts of cortisol 21-hexadecanoate were prepared essentially as described in Example 8. However, to simplify the interpretation of the DSC data, stearylamine acetate was omitted from those preparations, and distilled water was used as the aqueous medium for dispersing and washing. Di-(hexadecanoyl)phosphatidylcholine (14.9 mg.) was dissolved in chloroform (5 ml.) containing the weights of cortisol 21-hexadecanoate given in Table 5, in a 250 ml. round-bottomed flask. Liposomes were prepared and purified as in Example 8. After the second washing, the liposome plugs were separated from their supernatants, and the plugs were dried with intermittent mixing in a vacuum dessicator until the sample weights indicated that each one contained 50% by weight of water. These samples were then used for the DSC measurements.

The hydrated mixtures of phospholipid and steroid were prepared by intimately mixing powdered di-(hexadecanoyl)phosphatidylcholine (14.9 mg.) with the same weights of powdered cortisol 21-hexadecanoate as were used to prepare the liposomes. Each sample was then hydrated by adding a weight of distilled water equal to the total weight of phospholipid and steroid. These samples were then used for DSC measurements.

Differential scanning calorimetry was carried out on samples of equal weight hermetically sealed in suitable sample holders. Duplicate samples ("A" and "B" in Table 5 below) were run for each liposome and for each steroid lipid mixture. The spectrum between 0° C. and 80° C. was measured on a Perkin Elmer differential scanning calorimeter using a scan rate of 8° C. per minute.

Pure hydrated di-(hexadecanoyl)phosphatidylcholine undergoes two endothermic transitions: one at 35° C. (the pre-transition endotherm) and the other at 41° C. (the main transition endotherm). The mid peak width for the main transition is 3.0°–4.0° C. In the case of the abovementioned mixtures, the steroid had no effect on either the pre-transition endotherm or the main transition endotherm. By contrast, in the case of the abovementioned liposomes, the inclusion of steroid eliminated the pre-transition endotherm and caused the mid peak width of the main transition endotherm to increase as the concentration of steroid was increased (see Table 5). This increase was most marked up to 12 M% of steroid (1.66 mg.), and then showed little change at 21 M% of steroid (3.22 mg.). These differences between liposomes and simple mixtures show that at the concentration of steroid in liposomes quoted in Example 8, cortisol 21-hexadecanoate is directly associated with the di-(hexadecanoyl)phosphatidylcholine phase and therefore that liposomes act as a "carrier" for the steroid.

TABLE 5

| Weight of cortisol 21-hexadecanoate (mg.) | Mid peak width (°C.) | | | |
|---|---|---|---|---|
| | Liposomes | | Mixtures | |
| | A | B | A | B |
| 0 | 3.33 | 3.00 | 4.0 | 4.0 |
| 0.5 | 3.83 | 4.33 | 2.66* | 2.66* |

TABLE 5-continued

| Weight of cortisol 21-hexadecanoate (mg.) | Mid peak width (°C.) | | | |
|---|---|---|---|---|
| | Liposomes | | Mixtures | |
| | A | B | A | B |
| 1 | 5.99 | 6.66 | 4.00 | 4.00 |
| 1.66 | 6.99 | 8.99 | 4.00 | 4.00 |
| 3.22 | 6.33 | 6.66 | 4.33 | 4.00 |

*These particular results were anomalous, but the reason for this is not known.

EXAMPLE 20

Di-(hexadecanoyl)phosphatidylcholine (6 mg.) and cortisol 21-hexadecanoate (3 mg.) were dissolved in chloroform (1.24 ml.) containing phosphatidic acid (1 mg.). The chloroform was removed from the mixture by rotary evaporation in vacuo under nitrogen at a temperature of 61° C. [i.e. 20° above the phase transition temperature of di-(hexadecanoyl)phosphatidylcholine]. The dried lipid film was suspended in 5 mM phosphate-buffered saline (pH 7.4, 2 ml.), and the suspension was vigorously shaken at 61° C. for 15 minutes. The suspension was kept at 21° C. for one hour, and then washed three times with 5 mM phosphate-buffered saline (pH 7.4; 1 ml.) by centrifugation at 50,000 g for 10 minutes at 21°C., and then re-suspended in 5 mM phosphate-buffered saline (pH 7.4; 1 ml.). This liposome formulation was used in the experiments described in Examples 21 and 22.

EXAMPLE 21

A bilateral arthritis was induced in 18 Old English rabbits (average weight 2.05 kg.) by the intra-articular injection of poly-D-lysine (molecular weight 150,000; 7.5 mg.) and hyaluronic acid (7.5 mg.) in 0.95% w/v saline (1 ml.). A suspension of liposomes (made as described in Example 20) containing cortisol 21-hexadecanoate (a dose equivalent to 20 µg. of cortisol) was injected into one knee of the rabbits 4, 8 or 15 days after the injection of the poly-D-lysine/hyaluronic acid complex.

Joint temperature was measured with a Heinmann Radiation Thermometer at an ambient temperature of 19.5±0.5° C., and joint diameter with a Baty spring-loaded micrometer. The animals were killed three days after the liposome injection.

Results (a) Animals treated on Day 4

There was a marked, immediate decrease in the temperature of the treated knee compared with the untreated knee. This difference persisted for the 3 days after treatment. There was also a significant decrease in joint size, as shown by the joint diameter ratio, on treatment. This decrease persisted for the 3 days after treatment.

(b) Animals treated on Day 8

This treatment gave similar results to those described under (a) above. The change in joint temperature difference on treatment was not so great as in the animals treated on Day 4, and it occurred maximally 48 hours after the liposome injection. The temperature and joint size change persisted for the 3 days after treatment.

(c) Animals treated on Day 15

In this group there was only a slight change in the temperature of the treated knee, and the temperature difference between the treated and untreated knee was not maintained for the 3 days after treatment. The change in the joint diameter ratio on treatment was significantly less than that observed in the day 4 and day 8 treatment groups, and this change did not persist for the 3 days after treatment.

Conclusions

Of the three groups, the day 4 group showed the most favourable response. The amount of temperature reduction and joint size reduction indicated that the liposome preparation was therapeutically active. The response appeared to be lower in the Day 8 group, and almost absent in the Day 15 group.

EXAMPLE 22

A bilateral arthritis was induced in 18 male Old English rabbits as described in Example 21. The rabbits were then divided into three groups of six. Four days after the induction of arthritis:

(a) the rabbits in Group I received an intra-articular injection into the left knee only of a liposome suspension (prepared as described in Example 20) containing cortisol 21-hexadecanoate (at a dose equivalent to 20 µg. of cortisol);

(b) the rabbits in Group II received an intra-articular injection into the left knee only of a liposome preparation, prepared as described in Example 20 but containing no cortisol derivative; and (c) the rabbits in Group III received an intra-articular injection into the left knee only of a suspension of cortisol 21-acetate (at a dose equivalent to 20 µg. of cortisol). This suspension was prepared by shaking cortisol 21-acetate (at an amount equivalent to 20 µg. of cortisol) in pyrogen-free saline (B.P.; 0.5 ml.)

Joint temperature was measured with a Heinmann Radiation thermometer at an ambient temperature of 19.5±0.5° C. The diameters of the joints were measured with a Baty spring-loaded micrometer. Measurements were made daily for three successive days following the liposome injection.

Results

Neither the liposomes containing no cortisol derivative (Group II) nor the cortisol 21-acetate suspension (Group III) had any significant effect on the temperature or size of the injected joint. By contrast, in the animals in Group I there was a marked decrease in the temperature and size of the treated joint, compared with the untreated joint, which persisted for the three days of observation.

what we claim is:

1. A method for the treatment of inflammation at a site involving an enclosed cavity, in a host in need of such treatment, which comprises administering into said cavity an effective amount of a pharmaceutical composition comprising liposomes containing an anti-inflammatory corticosteroid bearing an 11-hydroxy substituent and bearing a lipophilic substituent which is attached by means of a carboxylic ester linkage to the residue of a hydroxy group which itself is attached to the 21-position of the corticosteroid, the said lipophilic substituent comprising an acyclic aliphatic chain of 15, 16 or 17 carbon atoms.

2. A method as claimed in claim 1 in which the enclosed cavity is a joint affected by rheumatic disease.

3. A method as claimed in claim 1 in which the anti-inflammatory corticosteroid bears a straight-chain alkanoyloxy substituent of 16 or 18 carbon atoms which is attached to the 21-position of said corticosteroid.

4. A method as claimed in claim 2 in which the anti-inflammatory corticosteroid bears a straight-chain alkanoyloxy substituent of 16 or 18 carbon atoms which is attached to the 21-position of said corticosteroid, and the composition is administered by intra-articular injection.

5. A method as claimed in claim 1 in which the anti-inflammatory corticosteroid is cortisol 21-hexadecanoate.

6. A method as claimed in claim 1 in which the anti-inflammatory corticosteroid is fluocinolone acetonide 21-hexadecanoate.

7. A method as claimed in claim 1 in which the anti-inflammatory corticosteroid is dexamethasone 21-hexadecanoate.

8. A method as claimed in claim 1 in which the anti-inflammatory corticosteroid is prednisolone 21-hexadecanoate.

* * * * *